United States Patent
Shade et al.

(10) Patent No.: US 10,125,658 B2
(45) Date of Patent: Nov. 13, 2018

(54) PARTICULATE SENSOR ASSEMBLY

(71) Applicant: Tenneco Automotive Operating Company Inc., Lake Forest, IL (US)

(72) Inventors: Benjamin C. Shade, Whitmore Lake, MI (US); Adam J. Kotrba, Laingsburg, MI (US)

(73) Assignee: Tenneco Automotive Operating Company Inc., Lake Forest, IL (US)

( * ) Notice: Subject to any disclaimer, the term of this patent is extended or adjusted under 35 U.S.C. 154(b) by 547 days.

(21) Appl. No.: 14/818,361

(22) Filed: Aug. 5, 2015

(65) Prior Publication Data

US 2017/0037754 A1    Feb. 9, 2017

(51) Int. Cl.

| | |
|---|---|
| *F01N 3/023* | (2006.01) |
| *F01N 11/00* | (2006.01) |
| *G01N 15/06* | (2006.01) |
| *F01N 13/00* | (2010.01) |
| *F01N 9/00* | (2006.01) |
| *F01N 3/10* | (2006.01) |
| *F01N 3/20* | (2006.01) |
| *F01N 3/021* | (2006.01) |
| *G01N 15/00* | (2006.01) |

(52) U.S. Cl.
CPC .......... *F01N 13/008* (2013.01); *F01N 9/002* (2013.01); *F01N 3/021* (2013.01); *F01N 3/103* (2013.01); *F01N 3/2066* (2013.01); *F01N 2560/05* (2013.01); *G01N 15/06* (2013.01); *G01N 2015/0046* (2013.01); *Y02T 10/47* (2013.01)

(58) Field of Classification Search
CPC .. G01N 15/06; G01N 2015/0046; F01N 3/21; F01N 3/023; F01N 3/2066; F01N 3/103; F01N 9/002; F01N 11/00; F01N 13/008; F01N 2560/05
USPC ............................................. 73/23.33, 28.01
See application file for complete search history.

(56) References Cited

U.S. PATENT DOCUMENTS

| | | |
|---|---|---|
| 6,367,320 B1 | 4/2002 | Kueper et al. |
| 7,628,007 B2 | 12/2009 | Kittelson et al. |
| 7,662,197 B2 | 2/2010 | Duvinags et al. |
| 7,685,814 B2 | 3/2010 | Zhang et al. |
| 7,739,898 B2 * | 6/2010 | Shaddock ............... F01N 13/08 73/23.31 |
| 7,832,254 B2 | 11/2010 | Guenschel et al. |
| 7,900,500 B2 | 3/2011 | Krafthefer |

(Continued)

FOREIGN PATENT DOCUMENTS

| | | |
|---|---|---|
| EP | 2143903 A1 | 1/2010 |
| JP | 2013083241 A | 5/2013 |

(Continued)

*Primary Examiner* — Daniel S Larkin

(74) *Attorney, Agent, or Firm* — Harness, Dickey & Pierce, P.L.C.

(57) ABSTRACT

A particulate sensor assembly may include a particulate sensor and a sensor housing. The particulate sensor may be configured to measure a quantity of particulate matter in a stream of exhaust gas from a combustion engine. The sensor housing may receive the particulate sensor and may include a cavity in which the particulate sensor is exposed to the exhaust gas. The cavity may be defined by a porous structure through which the exhaust gas may flow. The porous structure may filter a predetermined amount of particulate matter from the exhaust gas as the exhaust gas enters the cavity.

14 Claims, 2 Drawing Sheets

(56) References Cited

U.S. PATENT DOCUMENTS

| | | | |
|---|---|---|---|
| 8,310,249 | B2 | 11/2012 | Paterson |
| 8,447,461 | B2 | 5/2013 | Nevin et al. |
| 8,713,991 | B2 | 5/2014 | Allmendinger et al. |
| 8,769,937 | B2 | 7/2014 | Yanakiev et al. |
| 8,915,119 | B2 * | 12/2014 | Ueno ................... F01N 9/002 73/23.33 |
| 2008/0010975 | A1 | 1/2008 | Zhang et al. |
| 2008/0104946 | A1 | 5/2008 | Wang et al. |
| 2009/0241520 | A1 | 10/2009 | Gendron et al. |
| 2011/0047973 | A1 | 3/2011 | Wilhelm et al. |
| 2012/0186329 | A1 | 7/2012 | Yacoub et al. |
| 2012/0204537 | A1 | 8/2012 | Dea et al. |
| 2013/0318948 | A1 | 12/2013 | Van Marion |
| 2014/0182270 | A1 | 7/2014 | Jun |
| 2014/0202139 | A1 | 7/2014 | Qi et al. |
| 2014/0343747 | A1 | 11/2014 | Culbertson et al. |

FOREIGN PATENT DOCUMENTS

| | | |
|---|---|---|
| KR | 20120056601 A | 6/2012 |
| KR | 20130133020 A | 12/2013 |
| WO | WO-2013191698 A1 | 12/2013 |

\* cited by examiner

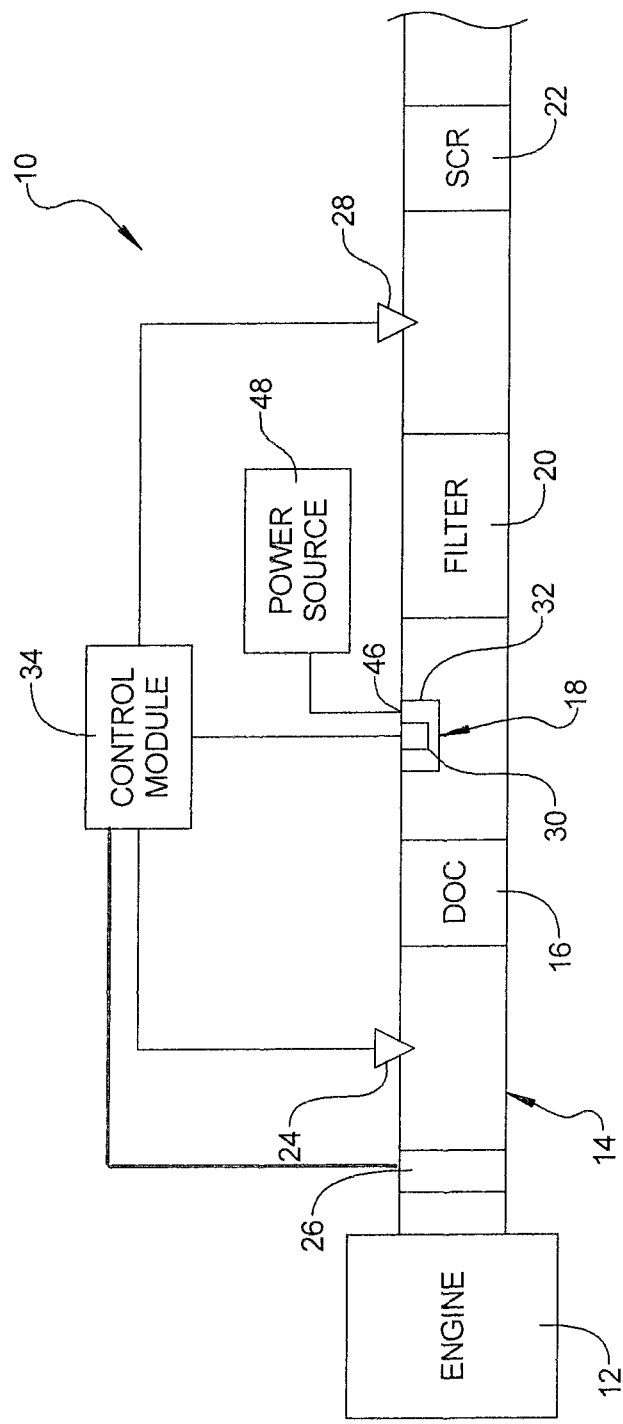

PARTICULATE SENSOR ASSEMBLY

FIELD

The present disclosure relates to a particulate sensor assembly for an exhaust aftertreatment system.

BACKGROUND

This section provides background information related to the present disclosure and is not necessarily prior art.

In an attempt to reduce the quantity of undesirable matter (e.g., $NO_x$, hydrocarbons, carbon monoxide, and/or particulate matter) discharged to the atmosphere during internal combustion engine operation, a number of exhaust aftertreatment devices have been developed. Typical aftertreatment systems for combustion engine exhaust may include an oxidation catalyst (e.g., a diesel oxidation catalyst or DOC), a particulate filter (e.g., a diesel particulate filter or DPF), a selective catalytic reduction (SCR) system, and/or other aftertreatment components.

Aftertreatment systems may include a particulate sensor mounted within an exhaust gas passageway. Such particulate sensors have been positioned downstream of the particulate filter and are typically used in conjunction with an onboard diagnostics system to detect a failure of the particulate filter. Therefore, unless the particulate filter has been cracked or otherwise damaged, these particulate sensors are exposed to exhaust gas having virtually no particulate matter. In the event of a cracked particulate filter, the particulate sensors are typically only exposed to very small amounts of particulate matter. Accordingly, typical particulate sensors are not designed to withstand prolonged exposure to exhaust gas with a high particulate matter concentration.

SUMMARY

This section provides a general summary of the disclosure, and is not a comprehensive disclosure of its full scope or all of its features.

In one form, the present disclosure provides a particulate sensor assembly that may include a particulate sensor and a sensor housing. The particulate sensor may be configured to measure a quantity of particulate matter in a stream of exhaust gas from a combustion engine. The sensor housing may receive the particulate sensor and may include a cavity in which the particulate sensor is exposed to the exhaust gas. The sensor housing may include a porous structure through which the exhaust gas may flow into the cavity. The porous structure may filter a predetermined amount of particulate matter from the exhaust gas as the exhaust gas enters the cavity.

In some configurations, the porous structure includes a metallic mesh.

In some configurations, the sensor housing includes a pair of electrical terminals selectively receiving electrical current that regenerates the metallic mesh.

In some configurations, the metallic mesh is coated with a catalytic material.

In some configurations, the sensor housing includes a main body formed from the metallic mesh and a boss extending from the main body, and wherein the particulate sensor extends through the boss and into the main body such that the cavity is defined by the main body and the particulate sensor.

In another form, the present disclosure provides an exhaust aftertreatment system that may include an exhaust gas passageway, a particulate filter, and a particulate sensor. The exhaust gas passageway receives exhaust gas from a combustion engine. The particulate filter is disposed within the exhaust gas passageway. The particulate sensor assembly may be disposed at least partially within the exhaust gas passageway upstream from the particulate filter. The particulate sensor assembly may include a particulate sensor and a sensor housing. The particulate sensor may be configured to measure a quantity of particulate matter in the exhaust gas. The sensor housing may receive the particulate sensor and may include a cavity in which the particulate sensor is exposed to the exhaust gas. The sensor housing may include a porous structure through which the exhaust gas may flow into the cavity. The porous structure may filter a predetermined amount of particulate matter from the exhaust gas as the exhaust gas enters the cavity.

In some configurations, the exhaust aftertreatment system includes a control module in communication with the particulate sensor. The control module may calculate a concentration of particulate matter in the exhaust gas upstream of the particulate filter based on the predetermined amount of particulate matter filtered by the sensor housing.

In some configurations, the control module selectively triggers a regeneration event to reduce a buildup of particulate matter on the porous structure.

In some configurations, the sensor housing includes a pair of electrical terminals selectively receiving electrical current. The regeneration event may include providing electrical current to the electrical terminals.

In some configurations, the porous structure includes a metallic mesh.

In some configurations, the sensor housing includes a pair of electrical terminals selectively receiving electrical current that regenerates the metallic mesh.

In some configurations, the metallic mesh is coated with a catalytic material.

In some configurations, the sensor housing includes a main body formed from the metallic mesh and a boss extending from the main body. The particulate sensor may extend through the boss and into the main body such that the cavity is defined by the main body and the particulate sensor. The boss may extend through an aperture in a wall of the exhaust gas passageway.

The particulate filter can be a diesel particulate filter, an SCR-coated diesel particulate filter or a gasoline particulate filter, for example.

In another form, the present disclosure provides a method that may include positioning a particulate sensor upstream of a particulate filter within an exhaust gas passageway; housing the particulate sensor within a porous structure; exposing the particulate sensor to exhaust gas within a cavity of the porous structure; filtering a predetermined amount of particulate matter from the exhaust gas prior to exposing the particulate sensor to exhaust gas; measuring, with the particulate sensor, an amount of particulate matter in the exhaust gas within the cavity; and determining a concentration of particulate matter in exhaust gas outside of the sensor housing upstream of the particulate filter based on the amount of particulate matter measured by the particulate sensor and the predetermined amount of particulate matter.

In some configurations, the method includes triggering a regeneration event to remove particulate matter built up on the porous structure.

In some configurations, triggering the regeneration event includes providing electrical current to a pair of terminals connected to the porous structure.

In some configurations, the method includes forming the porous structure from a metallic mesh.

In some configurations, the method includes coating the metallic mesh with a catalytic material.

The particulate filter can be a diesel particulate filter, an SCR-coated diesel particulate filter or a gasoline particulate filter, for example.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic representation of an exhaust aftertreatment system having a particulate sensor assembly according to the principles of the present disclosure;

Corresponding reference numerals indicate corresponding parts throughout the several views of the drawings.

DETAILED DESCRIPTION

Figure 3:
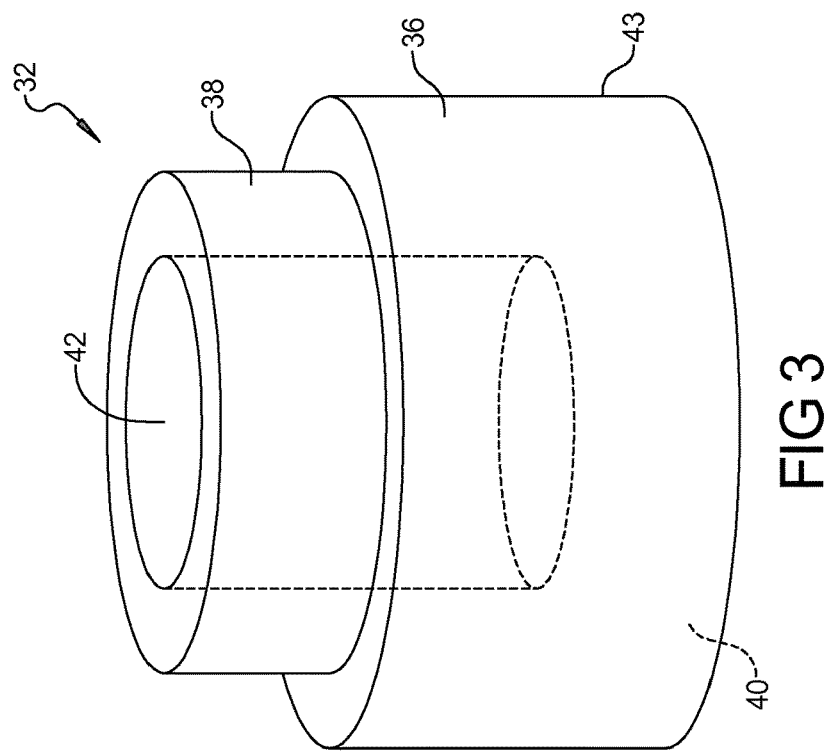
FIG. 3 is a schematic perspective view of a sensor housing of the particulate sensor assembly.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIG. 1, an exhaust aftertreatment system 10 is provided that may treat exhaust gas output by a combustion engine 12. The exhaust aftertreatment system 10 may include an exhaust gas passageway 14, an oxidation catalyst (e.g., a diesel oxidation catalyst or DOC) 16, a particulate sensor assembly 18, a particulate filter (e.g., a diesel particulate filter, an SCR-coated diesel particulate filter, or a gasoline particulate filter) 20 and a selective catalytic reduction (SCR) catalyst 22. The DOC 16, particulate filter 20 and SCR catalyst 22 are disposed within the exhaust gas passageway 14 and treat some or all of the exhaust gas output from engine 12 before the exhaust gas is discharged into the ambient environment.

A hydrocarbon (HC) injector 24 may be disposed at least partially within the exhaust gas passageway 14 upstream of the DOC 16. The HC injector 24 may receive hydrocarbon fuel from a fuel tank (not shown) and may inject the fuel into the stream of exhaust gas upstream of the DOC 16. A burner 26 may be disposed at least partially within the exhaust gas passageway 14 upstream of the DOC 16 at or adjacent the HC injector 24. The burner 26 may ignite the fuel injected by the HC injector 24 to regenerate the DOC 16 and/or the particulate filter 20.

A reductant injector 28 may be disposed at least partially within the exhaust gas passageway 14 downstream of the filter 20 and upstream of the SCR catalyst 22. The reductant injector 28 may receive a reductant (e.g., urea) from a reductant tank (not shown) and inject the reductant into the exhaust stream upstream of the SCR catalyst 22.

The particulate sensor assembly 18 may be disposed at least partially within the exhaust gas passageway 14 at a location upstream of the filter 20, for example. The particulate sensor assembly 18 could be disposed upstream or downstream of the DOC 16. The particulate sensor assembly 18 may include a particulate sensor 30 and a sensor housing 32. The particulate sensor 30 can be any type of sensor capable of measuring a particulate (or soot) mass or concentration in exhaust gas within the sensor housing 32. The particulate sensor 30 may be in communication with a controller or control module 34 that may receive the particulate mass or concentration values measured by the particulate sensor 30. As will be described in more detail below, the control module 34 may determine a particulate concentration of the exhaust gas in the exhaust gas passageway 14 upstream of the filter 20 based on the value measured by the particulate sensor 30. The control module 34 may also be in communication with and control operation of the HC injector 24, the burner 26, and the reductant injector 28.

Figure 2:
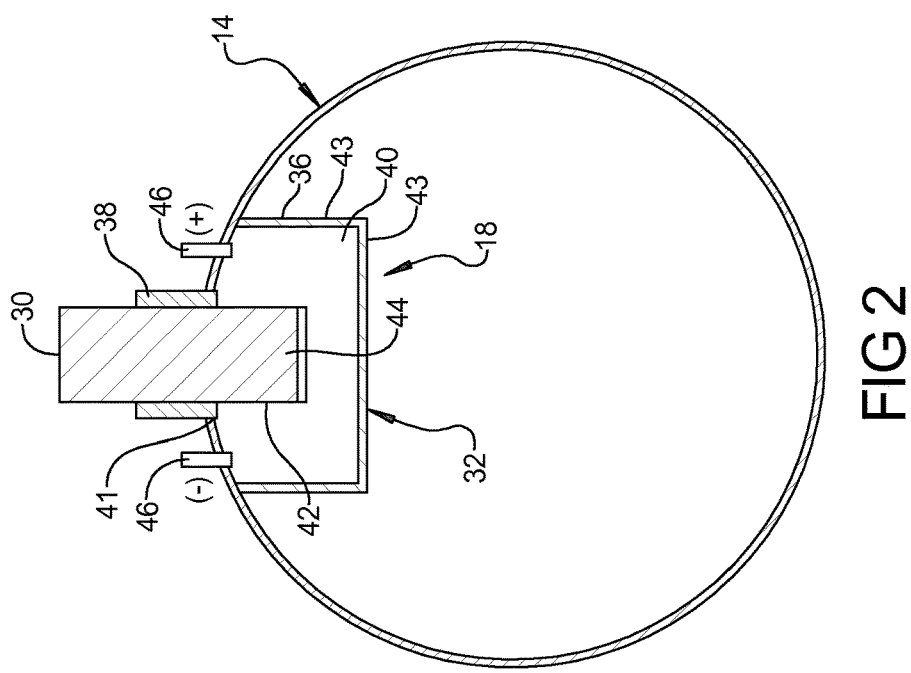
FIG. 2 is a schematic cross-sectional view of the particulate sensor assembly disposed partially within an exhaust gas passageway of the exhaust aftertreatment system.

Referring now to FIGS. 2 and 3, the sensor housing 32 may include a main body 36 and a boss 38 extending axially from an end of the main body 36. The main body 36 may define an internal cavity 40. A sensor pocket 42 may extend through the boss 38 and into the internal cavity 40. As shown in FIG. 2, the particulate sensor 30 may be received in the sensor pocket 42 such that at least a portion of the particulate sensor 30 is disposed within and in communication with the internal cavity 40.

As shown in FIG. 2, the sensor housing 32 may be mounted to the exhaust gas passageway 14 such that at least the main body 36 is disposed within the exhaust gas passageway 14 and exposed to exhaust gas flowing through the exhaust gas passageway 14. In some configurations, the boss 38 and a portion of the particulate sensor 30 may extend out of the exhaust gas passageway 14 through an aperture 41, as shown.

The main body 36 may be a porous or permeable structure formed from a metallic mesh, for example. In this manner, exhaust gas in the exhaust gas passageway 14 can flow into the internal cavity 40 through outer walls 43 of the main body 36. The sensor pocket 42 can be formed at least partially of a mesh structure, one or more ribs, or webbing, for example, or any other suitable structure, to allow at least an end 44 of the particulate sensor 30 to be directly exposed to the exhaust gas within the internal cavity 40. In some configurations, the particulate sensor 30 may be pressed into engagement with the boss 38 and/or otherwise secured thereto.

The porosity of the outer walls 43 of the main body 36 can be configured to filter a predetermined amount of particulate matter from the exhaust gas that passes therethrough. That is, the porous structure of the main body 36 can filter out a predetermined amount of particulate matter as exhaust gas flows through the outer walls 43 into the internal cavity 40 before coming into direct contact with the end 44 of the particulate sensor 30. The porosity of the main body 36 can be a function of an expected concentration of particulate matter in the exhaust stream of a particular engine 12. In some configurations, some or all of the main body 36 can be coated with a catalytic material.

As shown in FIG. 2, the sensor housing 32 can include electrical terminals 46 that may be in electrical communication with an electrical power source 48 (shown in FIG. 1) such as a battery, for example. The control module 34 can control a flow of electrical current between the power source 48 and the terminals 46.

With continued reference to FIGS. 1-3, operation of the system 10 will be described in detail. As described above, the particulate sensor assembly 18 may be positioned in a stream of exhaust gas in the exhaust passageway 14 upstream of the filter 20. The porous structure of the sensor housing 32 may filter a predetermined quantity of particulate matter from exhaust gas that flows through the outer walls 43 and into the internal cavity 40 of the sensor housing 32. The particulate sensor 30 may measure a quantity of particulate matter in the exhaust gas within the internal cavity 40 of the sensor housing 32 and communicate the measured value to the control module 34. The particulate sensor 30 may measure and communicate such values to the control module 34 continuously or intermittently.

The control module 34 may then calculate the concentration of particulate matter in the unfiltered exhaust gas upstream of the filter 20 outside of the sensor housing 32 based on the value measured by the particulate sensor 30 and the predetermined quantity of particulate matter filtered by the sensor housing 32. The control module 34 can utilize the calculated particulate concentration value to more precisely determine a solid carbon loading rate of the filter 20, for example.

Once a buildup of particulate matter on the sensor housing 32 reaches a predetermined level (i.e., once the porous structure of the sensor housing 32 is sufficiently loaded with particulate matter), the control module 34 may trigger a regeneration event to clean the buildup of particulate matter off of the sensor housing 32. This can be done by providing electrical current from the power source 48 to the terminals 46 to electrically heat the sensor housing 32 to burn off soot.

While the particulate sensor assembly 18 is described above as being disposed upstream of the filter 20, in some configurations, the particulate sensor assembly 18 could be incorporated into an exhaust aftertreatment system that does not include a particulate filter.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The descriptions above and accompanying figures serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A particulate sensor assembly comprising:
    a particulate sensor configured to measure a quantity of particulate matter in a stream of exhaust gas from a combustion engine; and
    a sensor housing receiving the particulate sensor and including a cavity in which the particulate sensor is exposed to the exhaust gas, the sensor housing includes a porous structure through which the exhaust gas may flow into the cavity, the porous structure filtering a predetermined amount of particulate matter from the exhaust gas as the exhaust gas enters the cavity, wherein the porous structure includes a metallic mesh, the sensor housing including a pair of electrical terminals selectively receiving electrical current that regenerates the metallic mesh.

2. The particulate sensor assembly of claim 1, wherein the metallic mesh is coated with a catalytic material.

3. The particulate sensor assembly of claim 2, wherein the sensor housing includes a main body formed from the metallic mesh and a boss extending from the main body, and wherein the particulate sensor extends through the boss and into the main body such that the cavity is defined by the main body and the particulate sensor.

4. An exhaust aftertreatment system comprising:
    an exhaust gas passageway receiving exhaust gas from a combustion engine;
    a particulate filter disposed within the exhaust gas passageway;
    a particulate sensor assembly disposed at least partially within the exhaust gas passageway upstream from the particulate filter, the particulate sensor assembly including a particulate sensor and a sensor housing, the particulate sensor configured to measure a quantity of particulate matter in the exhaust gas, the sensor housing receiving the particulate sensor and including a cavity in which the particulate sensor is exposed to the exhaust gas, the sensor housing includes a porous structure through which the exhaust gas may flow into the cavity, the porous structure filtering particulate matter from the exhaust gas as the exhaust gas enters the cavity;
    a control module in communication with the particulate sensor and calculating a concentration of particulate matter in the exhaust gas upstream of the particulate filter based on an amount of particulate matter filtered by the sensor housing, wherein the control module is operable to trigger a regeneration event to reduce a buildup of particulate matter on the porous structure.

5. The exhaust aftertreatment system of claim 4, wherein the sensor housing includes a pair of electrical terminals selectively receiving electrical current, and wherein the regeneration event includes providing electrical current to the electrical terminals.

6. The exhaust aftertreatment system of claim 4, wherein the porous structure includes a metallic mesh.

7. The exhaust aftertreatment system of claim 6, wherein the metallic mesh is coated with a catalytic material.

8. The exhaust aftertreatment system of claim 7, wherein the sensor housing includes a main body formed from the metallic mesh and a boss extending from the main body, wherein the particulate sensor extends through the boss and into the main body such that the cavity is defined by the main body and the particulate sensor, and wherein the boss extends through an aperture in a wall of the exhaust gas passageway.

9. The exhaust aftertreatment system of claim 4, wherein the particulate filter is one of a diesel particulate filter or a gasoline particulate filter.

10. A method comprising:
  positioning a particulate sensor upstream of a particulate filter within an exhaust gas passageway;
  housing the particulate sensor within a porous structure;
  exposing the particulate sensor to exhaust gas within a cavity of the porous structure;
  filtering particulate matter from the exhaust gas prior to exposing the particulate sensor to exhaust gas;
  measuring, with the particulate sensor, an amount of particulate matter in the exhaust gas within the cavity;
  determining a concentration of particulate matter in exhaust gas outside of the sensor housing upstream of the particulate filter based on the amount of particulate matter measured by the particulate sensor and a filtered amount of particulate matter; and
  triggering a regeneration event to remove particulate matter built up on the porous structure.

11. The method of claim 10, wherein triggering the regeneration event includes providing electrical current to a pair of terminals connected to the porous structure.

12. The method of claim 10, further comprising forming the porous structure from a metallic mesh.

13. The method of claim 12, further comprising coating the metallic mesh with a catalytic material.

14. The method of claim 13, wherein the particulate filter is one of a diesel particulate filter or a gasoline particulate filter.

* * * * *